United States Patent [19]
Rideout et al.

[11] Patent Number: 5,885,957
[45] Date of Patent: Mar. 23, 1999

[54] TREATMENT OF HTLV-I INFECTIONS

[75] Inventors: Janet Litster Rideout, Raleigh; David Walter Barry, Chapel Hill; Sandra Nusinoff Lehrman, Durham; Martha Heider St. Clair, Durham; Phillip Allen Furman, Durham, all of N.C.

[73] Assignee: Glaxo Wellcome Inc., Research Triangle Park, N.C.

[21] Appl. No.: 882,888

[22] Filed: Jun. 26, 1997

Related U.S. Application Data

[63] Continuation of Ser. No. 540,593, Feb. 26, 1993, Pat. No. 5,643,891, which is a continuation of Ser. No. 792,812, Nov. 15, 1991, abandoned, which is a continuation of Ser. No. 670,499, Mar. 15, 1991, abandoned, which is a continuation of Ser. No. 188,735, Apr. 29, 1988, abandoned, which is a continuation of Ser. No. 839,795, Mar. 14, 1986, abandoned.

[30] Foreign Application Priority Data

Mar. 16, 1985 [GB] United Kingdom ............... 8506869
May 9, 1985 [GB] United Kingdom ............... 8511774

[51] Int. Cl.$^6$ ............................ A61K 38/00; A61K 31/70
[52] U.S. Cl. ............................ 514/2; 514/50; 536/28.54; 530/351
[58] Field of Search ........................................... 514/2, 50

[56] References Cited

U.S. PATENT DOCUMENTS

| | | | |
|---|---|---|---|
| 3,660,564 | 5/1972 | Yoneda et al. | 514/85.6 |
| 4,360,522 | 11/1982 | Schaeffer | 514/262 |
| 4,649,140 | 3/1987 | Schaeffer | 514/261 |
| 4,695,570 | 9/1987 | Krenitsky | 514/261 |
| 4,723,242 | 2/1988 | Rideout et al. | 514/50 |
| 4,874,609 | 10/1989 | Rideout et al. | 424/85.4 |
| 5,521,161 | 5/1996 | Malley et al. | 514/45 |
| 5,643,891 | 7/1997 | Rideout et al. | 514/50 |

FOREIGN PATENT DOCUMENTS

| | | |
|---|---|---|
| 0 186 640 B1 | 7/1990 | European Pat. Off. . |
| 79/01068 | 12/1979 | WIPO . |

OTHER PUBLICATIONS

C.J. Krieg, et al., "Increase in Intracisternal A–Type Particles in Friend Cells During Inhibition of Friend Virus (SFFV) Release by Interferon or Azidothymidine," *Experimental Cell Research 116,* (1978) pp. 21–29.

W. Ostertag, et al., "Induction of Intracisternal A–Type Particles During Friend Cell Differentiation," *Experimental Cell Research 116,* (1978) pp. 31–37.

Donald E. Riesenberg, MD, "Anti–AIDS agents show varying early results in vitro and in vivo," *JAMA(Medical News)* Nov. 8, 1995–vol. 254, No. 18, pp. 2521, 2527 & 2529.

M. Anwar Waqar, et al., "Effect of 2',3'–Dideoxynucleosides on Mammalian Cells and Viruses," *Journal of Cellular Physiology* 121:402–408, 1984.

Ronald P. Glinski, et al., "Nucleotide Synthesis. IV.$^1$ Phosphorylated 3'–Amino–3'–deoxythymidine and 5'–Amino–5'–deoxythymidine and Derivatives$^{2,3}$," *J. Org. Chem.,* vol. 38, No. 25, 1975, pp. 4299–4305.

Ruth M. Ruprecht, et al., "Suppression of mouse viraemia and retroviral disease by 3'–azido–3'–deoxythymidine," *Nature,* vol. 323, Oct. 2, 1986, pp. 467–469.

Hiroaki Mitsuya, "3'–Azido–3'–deoxythymidine (BW A509U):An antiviral agent that inhibits the infectivity and cytopathic effect of human T–lymphotropic virus type III/lymphadenopathy–associated virus in vitro," *Proc. Natl. Acad. Sci USA,* vol. 82, pp. 7096–7100, Oct. 1985.

Parkash S. Gill, M.D., et al., "Treatment of Adult T–Cell Leukemia–Lymphoma With a Combination of Interferon Alfa and Zidovudine," *The New England Journal of Medicine,* pp. 1744–1748, Jun. 29, 1995, vol. 332, No. 26.

Olivier Hermine, M.D., et al, Brief Report: Treatment of Adult T–Cell Leukemia–Lymphoma with Zidovudine and Interferon Alfa, *The New England Journal of Medicine,* vol. 332, No. 26, pp. 1749–1751, Jun. 29, 1995.

Lin et al., "Synthesis and Biological Activity of Various 3'–Azido and 3'–Amino Analogues of 5–Substituted Pyrimidine Deoxyribonucleosides," *J. Medicinal Chem.,* 26(12), 1691–1696 (Dec. 1983).

Ostertag et al., "Induction of Endogenous Virus and of Thymidine Kinase by Bromodeoxyuridine Cell Cultures Transformed by Friend Virus," *Proc. Nat. Acad. Sci. USA,* 71(12), 4980–4985 (Dec. 1974).

Horwitz et al., "Nucleosides. V. The Monomesylates of 1–(2'–Deoxy–β–D–lyxofuranosyl)thymine," *J. Organic Chem.* 29, 2076–20–78 (Jul. 1964).

Vila et al., "Absence of Viral Rebound After Treatment of HIV–Infected Patients with Didanosine and Hydroxycarbamide," *The Lancet,* 350, 635–636 (Aug. 30, 1997).

*Primary Examiner*—Marian C. Knode
*Assistant Examiner*—L. Eric Crane
*Attorney, Agent, or Firm*—Karen L. Prus

[57] ABSTRACT

Treatment of animals or humans carrying or infected with HTLV-I, HTLV-I (including HTLV-I-associated leukemias or lymphomas), non-A, non-B hepatitis virus, hepatitis B virus, EBV, equine infectious anaemia or other lentiviruses or having antibodies to said viruses is disclosed using the compound 3'-azido-3'-deoxythymidine or a pharmaceutically acceptable basic salt thereof.

Also disclosed is the use of the 5'-mono-, di- and triphosphate of 3'-azido-3'-deoxythymidine or a pharmaceutically acceptable basic salt thereof for the same purpose.

2 Claims, No Drawings

TREATMENT OF HTLV-I INFECTIONS

This application is a continuation of U.S. Ser. No. 08/540,593, filed Feb. 26, 1993, now U.S. Pat. No. 5,643,891, which is a continuation of U.S. Ser. No. 07/792,812, filed Nov. 15, 1991, now abandoned, which is a continuation of U.S. Ser. No. 07/670,499, filed Mar. 15, 1991, now abandoned, which is a continuation of U.S. Ser. No. 07/188,735, filed Apr. 29, 1988, now abandoned, which is a continuation of U.S. Ser. No. 06/839,795, filed Mar. 14, 1986, now abandoned.

This invention is directed to the treatment of humans infected with HTLV-I and HTLV-II, including HTLV-I-associated leukemias and lymphomas, non-A, non-B hepatitis virus, hepatitis B virus, and Epstein-Barr virus (EBV), as well as to the treatment of animals infected with equine infectious anaemia and other lentiviruses.

It has now been discovered that the compound known as 3'-azido-3'-deoxythymidine having the formula I

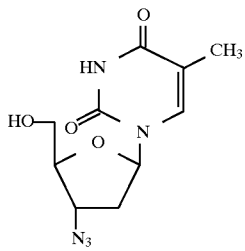

is useful in treating humans identified as having HTLV-I and HTLV-II infection, including HTLV-I-associated leukemias or lymphomas, non-A, non-B hepatitis, hepatitis B, or EBV infections. It is also useful in treating animals identified as having equine infectious anaemia or other lentivirus infections.

The compound of formula I may be administered perse or in the form of a pharmaceutically acceptable salt to the infected animal or human, e.g., an alkali metal salt such as sodium or potassium salts, an alkaline earth metal salt or an ammonium salt such as tetraalkylammonium salts (all of which are hereinafter referred to as a pharmaceutically acceptable base salt).

The salts of the compound of formula I convert to the compound per se after being administered. The compound 3'-azido-3'-deoxythymidine penetrates into the virally infected cells after contacting same and is converted by cellular enzymes to the monophoschate thereof. The monophosphate is then converted by the cellular enzymes to the diphosphate of the compound of formula I and ultimately to the triphosphate of the compound of formula I.

The triphosphate of the compound of formula I acts after contact with the virus to prevent replication of the virus.

Thus the compound of formula I can be said to be a pro-drug after entering the animal or human cells since it is an intermediate (precursor) to the 5'-mono-, di- and triphosphate thereof.

It is believed that the 5'-mono-, di- and triphosphates of the compound it of formula I can also be said to be prodrugs since they would invariably (at least in part) be hydrolized in the animal or human to 3'-azido-3'-deoxythymidine which is taken up by the cells.

As another feature of this invention, there is also disclosed the method of administering to an animal or human in need thereof the 5'-mono-, di, or triphosphate of the compound of formula I or their pharmaceutically acceptable base salts (i.e., alkali metal, alkaline earth or ammonium salt) to treat the above-mentioned virus infections and to inhibit the replication of the virus in infected animal or human cells. The 5'-mono-, di- and triphosphates of 3'-azido-3'-deoxythymidine are of the formulas II, III and IV respectively.

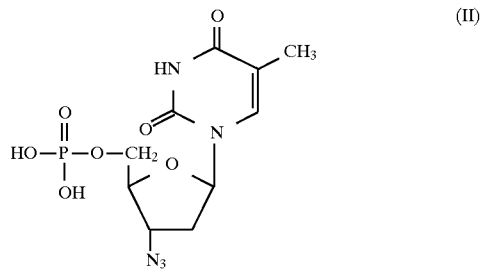

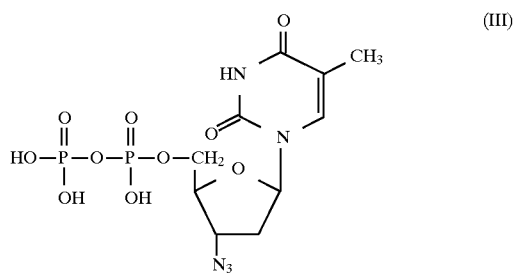

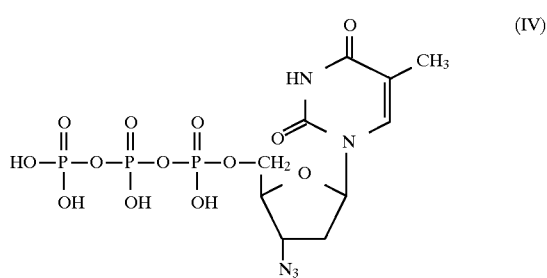

The present invention thus discloses compounds of formulas I, II, III and IV and their appropriate salts for use in the treatment of the conditions referred to above, as well as the use of such compounds in the preparation of pharmaceutical formulations for the treatment of such conditions. The above mentioned pharmaceutically acceptable salts may be prepared in a conventional manner, e.g., treatment of the compound with an appropriate base.

In general for the treatment of the above mentioned virus infections, a suitable effective dose of the 3'-azido-3'-deoxythymidine, its pharmaceutically acceptable basic salts, its mono-, di- or triphosphates or their pharmaceutically acceptable basic salts (all of which are hereinafter referred to as the administered ingredient) will be in the range 10 to 250 mg per kilogram body weight per day, preferably in the range of 25 to 100 mg per kilogram body weight per day and most preferably in the range 30 to 60 mg per kilogram body weight per day. The desired dose is preferably presented as two, three, four or more sub-doses administered at appropriate intervals throughout the day. These sub-doses may be administered at unit dosage forms, for example, containing 5 to 500 mg, preferably 10 to 200 mg and most preferably 20 to 100 mg of active ingredient per unit dosage form.

Administration may be by any suitable route including oral, rectal, nasal, topical (including buccal and sublingual), vaginal and parenteral (including subcutaneous, intramuscular, intravenous and intradermal) with oral or parenteral being preferred. It will be appreciated that the preferred route may vary with, for example, the condition and age of the recipient.

A preferred dose is administered to achieve peak plasma concentrations of the compound of formula I, its mono-, dior triphosphate or its pharmaceutically acceptable salts of from about 1 to about 100 μM, preferably about 2 to 80 μM, most preferably about 3 to about 50 μM. This may be achieved, for example, by the intravenous injection of a sterile 0.1 to 5% solution of the administered ingredients in saline as a bolus containing about 1 to about 40 mg/kg of the active ingredient. Desirable blood levels may be maintained by a continuous infusion to provide about 0.03 to about 1.0 mg/kg/hour or by intermittent infusions providing about 0.12 to about 30 mg/kg of the administered ingredient.

The administered ingredients may be used in therapy in conjunction with other medicaments such as 9-[[2-hydroxy-1-(hydroxymethyl)ethoxyl]methyl]-guanine, 9-(2-hydroxyethoxymethyl)guanine (acyclovir), 2-amino-9-(2-hydroxyethoxymethyl)purine, suramin, ribavirin, antimoniotungstate (HPA-23), interferon, e.g., a interferon, interleukin II, and phosphonoformate (Foscarnet) or in conjunction with other immune modulation including bone marrow or lymphocyte transplants or medications such as levamisol or thymosin which would increase lymphocyte numbers and/or function as is appropriate.

The compound of formula I, 3'-azido-3'-deoxythymidine, (sometimes also referred as azidothymidine) is disclosed in J. R. Horwitz et al, *J. Org. Chem.*, 29 Jul., 1964, pp. 2076–2078; M. Imazawa et al, *J.Org. Chem.*, 43(15) 1978, pp. 3044–3048; also see *Biochemical Pharmacology*, Vol. 29, pp. 1849–1851; C. J. Kreig et al, *Experimental Cell Research* 116 (1978) pp. 21–29. Also see W. Ostertag et al, *Proc.Nat.Acad.Sci. USA* 71 (1974) for some of its biological activities.

While it is possible for the administered ingredients to be administered alone, it is preferable to present them as part of a pharmaceutical formulation. The formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets, sustained release capsules, and may be prepared by any methods well known in the art of pharmacy.

Such methods include the step of bringing into association the to be administered ingredients with the carrier which constitutes one or more accessory ingredients. In general, the formulations are prepared by uniformly and intimately bringing into association the active ingredient with liquid carriers or finely divided solid carriers or both and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration in the mouth include lozenges comprising the ingredients in a flavoured basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered and a pharmaceutically acceptable carrier.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended animal or human; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients particularly mentioned above the formulations of this invention may include other agents conventional in the art having regard to the type of formulation in question, for example, those suitable for oral administration may include flavouring agents.

The $LD_{50}$ for 3'-azido-3'-deoxythymidine in mice and rats was found to be greater than 750 mg/kg.

The following examples illustrate the invention.

EXAMPLE 1

Preparation of 2,3'-Anhydrothymidine

Thymidine (85.4 g; 0.353 mol) was dissolved in 500 mL dry DMF (dimethyl formamide) and added to N-(2-chloro-1,1,2-trifluoroethyl)diethylamine (100.3 g; 0.529 mol) [prepared according to the method of D. E. Ayer, *J.Med. Chem.* 6, 608 (1963)]. This solution was heated at 70° C. for 30 minutes then poured into 950 mL ethanol with vigorous stirring. The product precipitated from this solution and was filtered. The ethanol supernatant was refrigerated then filtered to yield a total of 47.75 g (0.213 mol; 60.3%) of 2,3'-anhydrothymidine, mp=228°–230° C.

EXAMPLE 2

Preparation of 3'-Azido-3'-deoxythymidine 2,3'-Anhydrothymidine (25 g; 0.1115 mol) and $NaN_3$ (29 g; 0.446 mol) was suspended in a mixture of 250 mL DMF and 38 mL $H_2O$. The reaction was refluxed for 5 hours at which time it was poured into 1 liter of $H_2O$. This aqueous solution was extracted with ethyl acetate (EtOAc) (3×700 ml). The EtOAc was dried over $Na_2SO_4$, filtered, and then EtOAc was removed in vacuo to yield a viscous oil. This oil was stirred with 200 mL water resulting in a solid, 3'-azido-3'-deoxythymidine, 9.15 g (0.0342 mol; 30.7%) mp=116°–118° C.

EXAMPLE 3

Preparation of Sodium Salt of 3'-Azido-3'-deoxythymidine

Approximately one gram of 3'-azido-3'-deoxythymidine was dissolved in 50 mL of distilled water. The pH was adjusted to 12 with 1N NaOH. Approximately half of the solution was freeze dried. A white powder, the sodium salt of 3'-azido-3'-deoxythymidine as the 0.6 hydrate, 0.415 g, resulted.

Analysis calculated for $C_{10}H_{12}N_5NaO_4 \cdot 6/10\ H_2O$. Calculated: C,40.03; H,4.43; N,23.34; Na,7.66; Found: C,39.88; H,4.34; N,23.29; Na,7.90

EXAMPLE 4

Preparation of 5'-Monophosphate of 3'-Azido-3'-deoxythymidine

3'-Azido-3'-deoxythymidine (0.5 g, 1.87 mmol) was dissolved in 5 mL of triethyl phosphate and the mixture was cooled to –5° C. Phosphorus oxychloride (0.685 mL, 7 mmol) was added in one portion to the rapidly stirred solution which was then maintained at –10° C. for 22 hours. An aliquot was removed and added to concentrated ammonium hydroxide. Analysis of this sample on TLC (cellulose, n-PrOH:H20, 7:3 v/v) showed no remaining starting material and a single fluorescent spot with lower mobility than the nucleoside. The reaction mixture was poured onto 20 mL of ice and water. This was placed in an ice bath and the pH of the solution was adjusted to a value of 7.5 by the addition of 2N NaOH. The basic mixture was extracted once with chloroform and once with ether. The aqueous layer was again adjusted to give a pH of 7.5 and concentrated in vacuo to remove residual organic solvent. The material was stored at –10° C. until purified as follows:

Deactivated charcoal was prepared by washing coconut charcoal (50–200 mesh, 100 g) with 500 mL of 1 N HCl, 3 L of water, 35 mL of 3% toluene in 95% ethanol, 600 mL of 95% ethanol and finally extensively with water. Deactivated charcoal (12 mL of settled wet charcoal) was added with stirring to the monophosphate solution (0.72 g, 1.8 mmol, 30 mL). The supernatant was decanted and the charcoal was washed with 150 mL of water. The nucleotide was eluted from the charcoal by washing with 120 mL of 1.5M ammonium hydroxide In 50% ethanol. This solution was filtered through a 0.22 micron filter, concentrated in vacuo to 10 mL, filtered through a Amicon Centriflo CF-25 membrane, and lyophilized. The yield of diammonium 3'-azido-3'-deoxythymidine-5'-monophosphate was 0.36 g (0.94 mmol, 52%). This compound was characterized as a nucleoside 5'-monophosphate by the ability of 5'-nucleotidase to degrade it to the nucleoside.

EXAMPLE 5

Preparation of the 5'-Di- and Triphosohate of 3'-Azido-3'-deoxythymidine

The di- and triphosphate of 3'-azido-3'-deoxythymidine were prepared from the ammonium salt of the 5'-monophosphate of 3'-azido-3'-deoxythymidine by a four step sequence.

Step I—Preparation of Bis-(Tri-n-butylammonium) Pyrophosphate

A column of DOW 50 pyridinium resin was prepared by pouring 40 mL of resin into a 25 cm diameter column and washing with water until no more color eluted. Sodium pyrophosphate decahydrate (1.12 g, 2.51 mol) was dissolved in 30 mL of water and applied to the column. The column was eluted with water. A 125 mL fraction of the eluant which contained UV absorbing material was collected. The volume was reduced to 10 mL in vacuo and tri-n-butyl amine (1.2 mL) was added. The volume was reduced in vacuo and the residue was dried by coevaporation with pyridine four times. The product was stored in a freezer (–5° C.).

Step II—Preparation of the Acid Form of the 5'-Monophosphate of 3'-Azido-3-deoxythymidine The acid form of the monophosphate was prepared by passing the ammonium salt (0.1 g, 0.283 mmol) dissolved in 6 mL of water, through a 1.5 mL (10 eq.) column of DOW 50 $H^+$.

Step III—Preparation of Phosphoromorpholidate Derivative

The hydrogen form of the monophosphate, 0.283 mMol, was dissolved in 9 mL of water. Morpholine (99 μL, 1.13 mmol, 4 eq.) was added and the solution heated to reflux. Dicyclohexyl carbodiimide (0.234 g, 1.13 mmol, 4 eq.) dissolved in t-butanol (5 mL) was added over a three-hour period. The reaction was refluxed overnight. The reaction was cooled to room temperature, filtered, and the solvents removed in vacuo. Ethanol was added and evaporated in vacuo four times. The residue was dissolved in methanol and the phosphoromorpholidate precipitated by the addition of ether. The precipitate was triturated with ether four times and dried on a rotary evaporator. A yield of 97 mg, 50%, was obtained.

Step IV—Preparation of the 5'-Di- and Triphosphates of 3'-Azido-3'-deoxythymidine The phosphoromorpholidate derivative was dried by removal of pyridine in vacuo four times. The bis-(tri-n-butylammonium) pyrophosphate was also dried by removal of pyridine in vacuo. The phosphoromorpholidate was dissolved in pyridine, 5 mL, and added to the vessel containing the. pyrophosphate reagent. The reaction was allowed to continue overnite at room temperature. The pyridine was removed in vacuo. Water was added to the residue and removed in vacuo three times. The residue was frozen.

The reaction mixture (0.09 g) was thawed and dissolved in 50 mL of water. The solution was applied to a column (1×10 cm) of DEAE Sephadex A-25 which had been equilibrated with 50 mM ammonium bicarbonate. The phosphates were eluted with a 300 mL linear gradient of 50–800 mM ammonium bicarbonate. The fractions containing the diphosphate nucleotide were pooled as were those containing the triphosphate nucleotide. The pooled diphosphate and triphosphate fractions were each dried in vacuo, redissolved in water, dried again, redissolved in water and and lyophilized. The yields were: the diphosphate as the triammonium salt, 0.014 g; the triphosphate, as the tetrammonium salt, 0.002 g.

EXAMPLE 6

Enzymatic Synthesis of the 5'-Triphosphate of 3'-Azido-3'-deoxythymidine

The 5'-triphosphate was synthesized from the 5'-diphosphate using pyruvate kinase and nucleoside diphosphate kinase. The reaction mixture contained: 6 mM 3'-azido TDP, 12 mM adenosine triphosphate, 40 mM MgCl2, 40 mM potassium piperazine-N,N'-bis(2-ethanesulfonic acid) (PIPES buffer, pH 6.8), 30 mM phosphoenolpyruvate, 40 IU/ml nucleoside diphosphate kinase and 100 IU/ml pyruvate kinase in a final volume of 5 mL. The reaction mixture was incubated at 37° C. for 5 days. The reaction mixture was applied to a column (2.5×10 cm) of DEAE Sephadex A-25 which had been equilibrated with ammonium bicarbonate. The nucleotides were eluted with a gradient of 100–1000 mM ammonium bicarbonate. Fractions containing the triphosphate were pooled, and evaporated to dryness in vacuo. The compound was further purified using a preparative HPLC column (Whatman, Inc., Magnum 9 SAX) eluted with a gradient of 10–1000 mM potassium phosphate, ph 3.5. The resulting compound was further purified using a DEAE Sephadex A-25 column as above. The fractions containing the tetrammonium 3'-azido-3'-deoxy-thymidine-5'-triphosphate were pooled, dried in vacuo, redissolved in water and lyophilized to yield 0.008 g (0.01 mmol).

EXAMPLE 7

| Tablet Formulation | |
|---|---|
| 3'-Azido-3'-deoxythymidine | 100 mg |
| Lactose | 200 mg |
| Starch | 50 mg |
| Polyvinylpyrrolidone | 5 mg |
| Magnesium stearate | 4 mg |
| | 359 mg |

Tablets were prepared from the foregoing ingredients by wet granulation followed by compression.

EXAMPLE 8

Capsule

A two part soft gelatin is prepared by placing the tablet formulation of Example 7 in a two part capsule.

EXAMPLE 9

| Sterile Injectable Formulation | |
|---|---|
| 3'-Azido-3'-deoxythymidine | 0.125 g |
| Sterile, pyrogen-free, pH 7 phosphate buffer, q.s. to | 25 ml |

The formulation is sterilized by heat and then placed in a sealed container, e.g., glass, so that it may be administered by infusion or by injection.

EXAMPLE 10

The acid forms of the 5'-mono-, di- and triphosphate nucleotides of 3'-azido-3'-deoxythymidine are prepared by passing the corresponding ammonium salts through DOW 50 H+ columns and lyophilizing the solutions obtained thereby.

We claim:

1. A method of treating a human infected with HTLV-I comprising administering to said human an effective treatment amount of 3'-azido-3'-deoxythymidine, or a pharmaceutically acceptable salt thereof, or the 5'-mono-, di- or triphosphate thereof or a pharmaceutically acceptable salt of said phosphate, in combination with an interferon.

2. The method of claim 1 wherein the interferon is α-interferon.

* * * * *